United States Patent
Kadzai

(10) Patent No.: US 11,642,305 B2
(45) Date of Patent: May 9, 2023

(54) COMPOSITION FOR A SKIN AND HAIR PRODUCT

(71) Applicant: Melissa Kadzai, Chicago, IL (US)

(72) Inventor: Melissa Kadzai, Chicago, IL (US)

( * ) Notice: Subject to any disclaimer, the term of this patent is extended or adjusted under 35 U.S.C. 154(b) by 0 days.

(21) Appl. No.: 17/831,207

(22) Filed: Jun. 2, 2022

(65) Prior Publication Data

US 2022/0387297 A1    Dec. 8, 2022

Related U.S. Application Data

(60) Provisional application No. 63/196,606, filed on Jun. 3, 2021.

(51) Int. Cl.
| | | |
|---|---|---|
| *A61K 8/9789* | (2017.01) | |
| *A61K 8/92* | (2006.01) | |
| *A61Q 7/00* | (2006.01) | |
| *A61Q 19/00* | (2006.01) | |
| *A61Q 5/12* | (2006.01) | |
| *A61K 8/34* | (2006.01) | |

(52) U.S. Cl.
CPC .............. *A61K 8/9789* (2017.08); *A61K 8/34* (2013.01); *A61K 8/922* (2013.01); *A61Q 5/12* (2013.01); *A61Q 7/00* (2013.01); *A61Q 19/00* (2013.01)

(58) Field of Classification Search
None
See application file for complete search history.

(56) References Cited

U.S. PATENT DOCUMENTS

| | | |
|---|---|---|
| 8,623,335 B2 | 1/2014 | Waddington |
| 10,307,366 B2 | 6/2019 | Brumbaugh |
| 10,434,052 B2 | 10/2019 | Hood |
| 10,722,461 B2 | 7/2020 | Burnam |
| 2017/0042784 A1 | 2/2017 | Munk |

*Primary Examiner* — Nannette Holloman

(57) ABSTRACT

A composition for a skin and hair product enhances the overall look of hair. The composition includes a quantity of aloe vera liquid, a quantity of marsh mallow root extract, a quantity of rosemary extract, a quantity of hydrolyzed wheat protein, a quantity of watermelon extract, a quantity of artichoke extract, a quantity of red clover extract, a quantity of lavender essential oil, a quantity of sandalwood essential oil, a quantity of *Hibiscus* extract, a quantity of orange essential oil, a quantity of preservative, a quantity of bamboo extract, a quantity of blue flax extract, a quantity of *Amaranthus* seed extract, a quantity of cedar essential oil, a quantity of geranium essential oil, a quantity of bergamot essential oil, a quantity of hydrolyzed quinoa protein, a quantity of hydrolyzed keratin protein, a quantity of apricot extract, a quantity of camelia seed oil, a quantity of marsh mallow oil, a quantity of honey extract, a quantity of panthenol, a quantity of vegetable glycerin, a quantity of solubilizer, a quantity of honey extract, and a quantity of chamomile extract. The composition is homogeneously mixed into a skin and hair product which may be applied to the hair or skin using a mister or aerosol delivery system or as a serum.

20 Claims, 1 Drawing Sheet

| % by weight | common name | concentration |
|---|---|---|
| 81.16 | aloe vera liquid | 100% fractionally distilled aloe vera liquid |
| 3.14 | Marsh mallow root extract | 2-3% concentration Marsh mallow Althea Ofiicinalis root extract |
| 1 | lavender essential oil | 25%-45% concentration Linalool, 20-40% concentration Linalyl acetate, and max 0.6% concentration camphor |
| 1.42 | hydrolyzed wheat protein | hydrolyzed wheat protein |
| 0.15 | chamomile extract | 20% concentration chamomille recutita matricaria flower extract |
| 0.21 | panthenol | D-pantothenyl alcohol |
| 0.07 | preservative | benzyl alcohol Dehydroacetic Acid |
| 0.22 | solubilizer | Polyglyceryl-6 Caprylate and Polyglyceryl-4 Caprate |
| 0.82 | sandalwood essential oil | 15 - 25% concentration z-α-Santalol |
| 0.1 | hydrolyzed keratin protein | 20-23% concentration hydrolyzed keratin protein |
| 0.24 | cedar essential oil | 6-20% concentration g-Himachalene and 29-52% concentration b-Himachalene |
| 0.08 | hydrolyzed quinoa protein | hydrolyzed quinoa protein |
| 0.14 | honey extract | propanediol, mel extract |
| 0.47 | blue flax extract | 20% linum alpinum flower extract |
| 0.08 | vegetable glycerin | 99.7% concentration vegetable glycerin |
| 4.14 | rosemary extract | 20% rosmarinus officinalis leaf extract |
| 0.2 | bergamot essential oil | 35-48% concentration limonene and 22-36% concentration linalyl acetate |
| 1.28 | watermelon extract | highly purified citrullus lanatus extract |
| 0.75 | hibiscus extract | 10:1 hibiscus extract and propanediol |
| 1 | red clover extract | 10:1 red clover extract and propanediol |
| 0.15 | marsh mallow oil | 10% concentration marsh mallow root/liter of extra virgin olive oil |
| 0.42 | amaranthus seed extract | amaranthus caudatus velvet flower seed extract |
| 1.17 | artichoke extract | cynara scolymus leaf extract |
| 0.21 | geranium essential oil | 25-36% concentration citronellol and 10-18% geraniol |
| 0.15 | camellia extract | 100% concentration camellia oleifera |
| 0.58 | orange essential oil | 93-96% concentration limonene |
| 0.17 | apricot extract | 10% concentration apricot seed extract |
| 0.48 | bamboo extract | 20% concentration bambusa vulgaris extract |

COMPOSITION FOR A SKIN AND HAIR PRODUCT

The current application claims a priority to the U.S. provisional patent application Ser. No. 63/196,606 filed Jun. 3, 2021.

FIELD OF THE INVENTION

The present invention relates generally to compositions of personal care products and more specifically it relates to multifunctional products for the skin and hair.

BACKGROUND OF THE INVENTION

People often experience thinning hair with aging. Thinning hair can be caused by hereditary traits, thyroid disorders, endocrine disorders, nutritional deficiencies, and reduced hormone support. Hair is composed of protein strands, and a single strand of hair lives two to seven years. On average, a healthy head of hair grows a minimum of half an inch a month and six inches in a year, but age, genetics, diet, and health of the person determine the overall health of the hair and how fast it grows. Often hair growth is nullified by damage created at the end of the hair strand and the hair must be cut in order to maintain hair health. Many hair products attempt to solve this issue by overloading their products with protein, but this can result in even more damage to the hair if misused or used improperly. Problems with hair can create insecurities in people. Problems such as stunted hair growth, hair breakage, dry and dull hair appearance leave people less confident about their appearance. Even unwanted hair style changes and limited hair styling time can make people less secure about their appearance.

The present invention solves many problems related to hair and skin. When used on hair, the composition for a skin and hair product speeds up hair growth, depending on individual use and factors such as age, genetics, diet, and overall health of the user. This, coupled with the limiting of breakage and shedding of the hair allows the user to go longer between haircuts to maintain overall hair health. An object of the present invention is to create a product that can be left on the hair for an extended period creating a youthful look and feel to the user's hair. Other products use oil-based products to attempt to create a youthful look. These products are impractical because they leave a sticky or heavy feeling to the user's hair. Other products are mostly water and leave the hair wet, not weightless. The composition for a skin and hair product uses aloe vera as a base to overcome these problems.

Another object of the current invention is to have improved hair styling features. The product has memory, in other words hair that the product is used on has air forming qualities and maintains an elastic-like benefit. There are heat activated features for flat ironing, and when the hair is curled the curls have spring and bounce. Less heat is needed to style the hair. The curls have the ability to withstand the elements such as sun, heat, humidity, and rain. The product gives weightless body, when sprayed on dry hair, the product gives weightless movement and body. The cuticle layer of the hair swells, giving the illusion of fuller, thicker hair. The present invention is volumizing for hair without a sticky feel, possibly allowing the avoidance of hair spray. The product gives impeccable shine without weighing the hair down. The present invention may be used as a dry shampoo due to hair reviving features. The product makes hair easier to detangle, style and manage. Style time is reduced, users can shampoo less frequently.

Another object of the present invention is to provide skin healing benefits such as calming down inflammation in the skin. The product hydrates and tones and reduces hyperpigmentation.

Another object of the present invention is to be multipurpose. There are many products on the market which are for skin or hair specifically, and users find that it is necessary to have a cabinet full of products in order to achieve a desired look.

BRIEF DESCRIPTION OF THE DRAWING

FIG. 1 is a table of the composition for a hair and skin product.

DETAIL DESCRIPTIONS OF THE INVENTION

All illustrations of the drawing are for the purpose of describing selected versions of the present invention and are not intended to limit the scope of the present invention.

The present invention is a composition for skin and hair product. The composition for a hair and skin product has the multifunctional ability to assist in day-to-day hair and skin maintenance and hair styling while providing the hair and skin with variations of nutrition and conditioning. The skin and hair product rejuvenates the hair and restores a more youthful look and feel by using aloe vera as a base. The composition for skin and hair product contains an optimal amount of various ingredients in order to create a skin and hair product that improves the appearance and feel of the user's hair.

This composition for a skin and hair product possibly slows down the process of aging and improves the elasticity of the hair. Furthermore, the skin and hair product may be used in place of a holding spray and helps restore elasticity in the hair and provides memory to the hair. The skin and hair product is a sun protectant and blocks humidity, reducing the effects of weather on a hairstyle. The molecules in the skin and hair product are small enough to penetrate the cuticle of the hair without wetting the hair.

The present invention is a Dihydrotestosterone blocker, which slows down the Dihydrotestosterone process. Dihydrotestosterone is a hormone linked to hair loss.

The present invention leaves hair bouncy and can be used on wet or dry hair. The skin and hair product works especially well on hair with texture. The skin and hair product restores curls and maintains the integrity of the strand of hair. The product allows styling with less heat and can take the place of multiple hair products.

The present invention may be used on skin to reduce inflammation and assist with wound healing. The product assists with eczema, dandruff, and skin issues in general.

Referencing FIG. 1, 100% fractionally distilled aloe vera liquid is hereinafter referred to as the common name aloe vera liquid. A 2-3% concentration Marsh mallow Althea Officinalis root extract is hereinafter referred to as the common name marsh mallow root extract. A 25%-45% concentration Linalool, 20-40% concentration Linalyl acetate, and max 0.6% concentration camphor is hereinafter referred to as the common name lavender essential oil. A 20% concentration chamomille recutita matricaria flower extract is hereinafter referred to as the common name chamomile extract. D-pantothenyl alcohol is hereinafter referred to as the common name panthenol. A 15-25% concentration z-α-Santalol is hereinafter referred to as the common name sandalwood essential oil. A 20-23% concentration hydrolyzed keratin protein is hereinafter referred to as the common name hydrolyzed keratin protein. A 6-20% concentration g-Himachalene and 29-52% concentration b-Himachalene is hereinafter referred to as the common name cedar essential oil. Propanediol, mel extract is hereinafter referred to as the common name honey extract. *Linum alpinum* flower extract is hereinafter referred to as the common name blue flax extract. A 99.7% concentration vegetable glycerin is hereinafter referred to as the common name vegetable glycerin. Rosmarinus officinalis leaf extract is hereinafter referred to as the common name rosemary extract. A 35-48% concentration limonene and 22-36% concentration linalyl acetate is hereinafter referred to as the common name bergamot essential oil. Highly purified *Citrullus lanatus* extract is hereinafter referred to as the common name watermelon extract. A 10:1 *Hibiscus* extract and propanediol is hereinafter referred to as the common name *Hibiscus* extract. A 10:1 red clover extract and propanediol is hereinafter referred to as the common name red clover extract. A 10% concentration marsh mallow root/liter of extra virgin olive oil is hereinafter referred to as the common name marsh mallow oil. *Amaranthus caudatus* velvet flower seed extract is hereinafter referred to as the common name *Amaranthus* seed extract. *Cynara scolymus* leaf extract is hereinafter referred to as the common name artichoke extract. A 25-36% concentration citronellol and 10-18% geraniol is hereinafter referred to as the common name geranium essential oil. A 100% concentration *Camellia oleifera* is hereinafter referred to as the common name *Camellia* extract. A 93-96% concentration limonene is hereinafter referred to as the common name orange essential oil. A 10% concentration apricot seed extract is hereinafter referred to as the common name apricot extract. A 20% concentration *Bambusa vulgaris* extract is hereinafter referred to as the common name bamboo extract.

Marsh mallow root extract is a high-purity extract from European marsh mallow roots. The plant is well-known for its anti-irritant, soothing and emollient properties. The extract concentration is 2-3% dissolved in water and glycerin.

Lavender essential oil is comprised of Linalool 25-45%, Linalyl acetate 20-40% and Camphor max 0.6%. The lavender plant is a woody evergreen shrub with pale green, narrow linear leaves and violet-blue flowers. The entire plant is covered with oil glands which cover the plant in star-shaped hairs. Lavender has been used since ancient times. Differences in soil, altitude, temperature, precipitation, and seasons contribute to subtle changes in the scent from one lot of Lavender essential oil to another.

Hydrolyzed wheat protein is a low molecular weight protein derived from soft wheat. It provides amino acids and high glutamine levels to skin and hair. It is gluten-free. It is composed of hydrolyzed wheat protein, water, benzyl alcohol, potassium sorbate, and sodium benzoate.

Chamomile extract is chamomile extract 20% in a base of glycerin and water. Chamomile extract is comprised of Chamomille Recutita (matricaria) flower extract, glycerin, water, and phenoxyethanol.

Panthenol is the alcohol analog of pantothenic acid (vitamin B5). Panthenol's activity is 75%. Panthenol is comprised of D-panthenol and water.

Sandalwood extract is comprised of 15-25% z-α-Santalol. The botanical name for sandalwood is *Santalum spicatum*. Some thirty species of sandalwood occur throughout Asia, Australia, and the Pacific region. This species is presently harvested in the Goldfields region of Western Australia. The evergreen is parasitic, burrowing its roots into nearby trees to sustain itself for the first seven years, leaving the other tree to die. To produce oil, the sandalwood tree must be over 30 years old.

Hydrolyzed keratin protein is sheep-wool derived. Keratin is a highly specialized fibrous protein which is found in hair, feathers, wool, and nails. Keratin is rich in cysteine, a sulfur-containing amino acid, which gives keratin a unique strength and protective quality. Hydrolyzed keratin protein contains 20-23% of protein. The molecular weight is 1,100-3,300 Da. It is gluten free.

Cedar essential oil is comprised of 6-20% concentration g-Himachalene and 29-52% concentration b-Himachalene. Cedarwood is a pyramid-shaped majestic evergreen tree which grows up to 131 feet high. The wood itself is hard and strongly aromatic, containing essential oil which is obtained by steam distillation.

Hydrolyzed quinoa protein is comprised of hydrolyzed quinoa protein, water, benzyl alcohol, potassium sorbate, and sodium benzoate. Hydrolyzed quinoa protein improves hair color and shine retention, protects hair and skin from environmental stress, and is very useful to moisturize and hydrate the skin.

Honey extract is comprised of Mel (honey) extract, water, propanediol, potassium sorbate, and sodium benzoate. Honey extract is a natural humectant and moisturizer able to retain moisture on the skin and hair.

Blue flax extract is an extract obtained from the leaves and stem of the *Linum alpinum* flower. Blue flax extract reduces skin irritation. Blue flax extract is prepared via a cold process to avoid potential loss of effectiveness from heat processing. Blue flax extract is dissolved in glycerin and water at a concentration of 20% blue flax concentrate and 80% diluents.

Rosemary leaf extract contains 20% extract dissolved in 80% glycerin and water. Rosemary leaf extract is prepared with a cold process to avoid potential loss of effectiveness from heat processing.

Bergamot essential oil is from the plant *Citrus bergamia*. The bergamot tree can grow up to four meters high, with star shaped flowers and smooth leaves, bearing *Citrus* fruit resembling a cross between an orange and a grapefruit. The oil is cold pressed from the fruit peel. Bergamot essential oil is comprised of 35-48% Limonene and 22-36% Linalyl acetate.

Watermelon extract is comprised of highly purified *Citrullus lanatus* fruit extract, glycerin, water, citrulline, phenoxyethanol, sodium benzoate, and potassium sorbate.

*Hibiscus* extract is a 10:1 extract liquid blend of *Hibiscus* extract and propanediol. This extract is obtained from the *Hibiscus syriacus* Linn botanical and offers powerful cleansing and intense moisturizing properties to hydrate and soften the skin.

Red clover extract is a 10:1 extract liquid blend of red clover extract and propanediol. Red clover extract has soothing, calming, and skin-softening properties. It also has anti-aging actions and stimulates activity on hair growth.

Marsh mallow oil is 100 grams of herb per 1000 ml of extra virgin olive oil. Marsh mallow oil has a unique demulcent nature and anti-inflammatory benefits. It has a protective and cooling effect on the scalp and hair, and soothes hydrates, and softens skin.

*Amaranthus* seed extract is naturally obtained peptides from the seeds of *Amaranthus caudatus* and contains 8-12% extracts dissolved in water. It is gluten free.

Artichoke leaf extract is obtained from the leaves of *Cynara scolymus* leaf. The extract's active ingredients are hydroxycinnamic derivatives. The artichoke leaf extract is dissolved in propanediol, water, and glycerin and also contains sodium benzoate, gluconolactone, and calcium gluconate as preservatives.

Geranium essential oil is steam distilled from the plant leaves of *Pelargonium roseum* x *asperum*. Geranium essential oil is comprised mainly of 26.8% citronellol and 23.6% geraniol.

*Camellia* extract is *Camellia* seed carrier oil. It is cold pressed from the seeds of *Camellia oleifera*, a wildflower which grows in China and Japan. *Camellia* extract contains antioxidants and helps to give a revitalized and rejuvenated look to skin and hair.

Orange essential oil is cold pressed from the fruit peel of *Citrus sinensis*. Orange essential oil is 93-96% limonene.

Apricot extract is comprised of 10% apricot seed extract and propanediol. Apricot extract is a rich source of vitamins C and A, which helps to remove buildup from the surface of the skin and to keep the skin well hydrated.

Bamboo extract is comprised of 20% *Bambusa vulgaris* extract, glycerin, water, and phenoxyethanol as a preservative. Bamboo extract has good moisturizing properties. The bamboo stems are high in silica deposits which give shininess, strength and smoothness to hair.

As seen in FIG. 1, the composition for skin and hair products comprises a quantity of watermelon extract, a quantity of aloe vera liquid, a quantity of lavender essential oil, a quantity of sandalwood essential oil, a quantity of bergamot essential oil, a quantity of bamboo extract, a quantity of *Hibiscus* extract, a quantity of rosemary extract, a quantity of red clover extract, a quantity of marsh mallow oil, a quantity of chamomile extract, a quantity of *Amaranthus* seed extract, a quantity of panthenol, a quantity of artichoke extract, a quantity of geranium essential oil, a quantity of camelia seed oil, a quantity of cedar essential oil, a quantity of orange essential oil, a quantity of hydrolyzed quinoa protein, a quantity of vegetable glycerin, a quantity of blue flax extract, a quantity of hydrolyzed keratin protein, a quantity of hydrolyzed wheat protein, a quantity of honey extract, a quantity of solubilizer, a quantity of preservative, a quantity of marsh mallow root extract, and a quantity of apricot extract mixed homogeneously. The solubilizer may be a quantity of Polyglyceryl-6 Caprylate and Polyglyceryl-4 Caprate in preferred embodiments. This solubilizer is a natural solubilizer derived from palm and canola raw materials. The solubilizer will allow the present invention to cleanse the hair of any dirt or debris while also acting as an emollient which will ensure that the hair retains its moisture. The preservative may be a quantity of benzyl alcohol Dehydroacetic Acid in preferred embodiments.

As shown in FIG. 1 the quantity of aloe vera liquid is approximately 81.16 percentage by weight (wt. %) of the composition of skin and hair product. Other compositional constituents are approximately 18.84 wt. %. A quantity of rosemary extract is approximately 4.14 wt. % of the skin and hair product. A quantity of marsh mallow root extract is approximately 3.14 wt. % of the skin and hair product. A quantity of hydrolyzed wheat protein is approximately 1.42 wt. % of the skin and hair product. A quantity of watermelon extract is approximately 1.28 wt. % of the skin and hair product. A quantity of artichoke extract is approximately 1.17 wt. % of the skin and hair product. A quantity of red clover extract is approximately 1.0 wt. % of the skin and hair product. A quantity of lavender essential oil is approximately 1.0 wt. % of the skin and hair product. A quantity of sandalwood essential oil is approximately 0.82 wt. % of the skin and hair product. A quantity of *Hibiscus* extract is approximately 0.75 wt. % of the skin and hair product. A quantity of orange essential oil is approximately 0.58 wt. % of the skin and hair product. A quantity of preservative is approximately 0.07 wt. % of the skin and hair product. A quantity of bamboo extract is approximately 0.48 wt. % of the skin and hair product. A quantity of blue flax extract is approximately 0.47 wt. % of the skin and hair product. A quantity of *Amaranthus* seed extract is approximately 0.42 wt. % of the skin and hair product. A quantity of cedar essential oil is approximately 0.24 wt. % of the skin and hair product. A quantity of geranium essential oil is approximately 0.21 wt. % of the skin and hair product. A quantity of bergamot essential oil is approximately 0.20 wt. % of the skin and hair product. A quantity of hydrolyzed quinoa protein is approximately 0.08 wt. % of the skin and hair product. A quantity of hydrolyzed keratin protein is approximately 0.10 wt. % of the skin and hair product. A quantity of apricot extract is approximately 0.17 wt. % of the skin and hair product. A quantity of camelia seed oil is approximately 0.15 wt. % of the skin and hair product. A quantity of marsh mallow oil is approximately 0.07 wt. % of the skin and hair product. A quantity of honey extract is approximately 0.14 wt. % of the skin and hair product. A quantity of panthenol is approximately 0.21 wt. % of the skin and hair product. A quantity of vegetable glycerin is approximately 0.08 wt. % of the skin and hair product. A quantity of solubilizer is approximately 0.22 wt. % of the skin and hair product. A quantity of honey extract is approximately 0.14 wt. % of the skin and hair product. A quantity of chamomile extract is approximately 0.15 wt. % of the skin and hair product. In reference to the aforementioned compositional proportions, the term "approximately" preferably means within an error range of up to ±0.005 wt. %.

The skin and hair product may be applied to the hair or skin using a sprayer or aerosol delivery system or topically as a serum. Sprayers and aerosol delivery systems are well known in the prior art. A sprayer is composed of a dust cap; an actuator; an insert; a closure; a gasket; a mechanism including a piston, stem, seal, spring, and housing cap; and a dip tube. Pressing the actuator draws the product up the dip tube, through the piston toward the actuator where the product exits the insert. Aerosol spray creates a mist of liquid particles. An aerosol sprayer is composed of a can or bottle which contains a payload, and a propellant under pressure. When a valve on the container is opened, the payload is forced out of a small opening as an aerosol or mist. A serum is a skin or hair care product that is designed to deliver high concentrations of specific active ingredients to the skin or hair respectively.

Although the invention has been explained in relation to its preferred embodiment, it is to be understood that many other possible modifications and variations can be made without departing from the spirit and scope of the invention as hereinafter claimed.

What is claimed is:

1. A composition for a skin and hair product, the composition consisting essentially of:
a combination of a predefined quantity of 100% concentration fractionally distilled aloe vera liquid; a predefined quantity of 2-3% concentration Marsh mallow Althea Officinalis root extract; a predefined quantity of 25-45% concentration Linalool, 20-40% concentration Linalyl acetate, and Max 0.6% concentration Camphor; a predefined quantity of Hydrolyzed wheat protein; a predefined quantity of 20% concentration Chamomille recutita matricaria flower extract; a predefined quantity of D-pantothenyl alcohol; a predefined quantity of preservative; a predefined quantity of solubilizer; a predefined quantity of 15-25% concentration z-α-Santalol; a predefined quantity of 20-23% hydrolyzed keratin protein; a predefined quantity of 6-20% concentration g-Himachalene and 29-52% concentration b-Himachalene; a predefined quantity of hydrolyzed quinoa protein; a predefined quantity of propanediol, mel extract; a predefined quantity of *Linum alpinum* flower extract; a predefined quantity of 99.7% concentration vegetable glycerin; a predefined quantity of Rosmarinus officinalis leaf extract; a predefined quantity of 35-48% limonene and 22-36% linalyl acetate; a predefined quantity of highly purified *Citrullus lanatus* extract; a predefined quantity of 10:1 *Hibiscus* extract and propanediol; a predefined quantity of 10:1 red clover extract and propanediol; a predefined quantity of 10% marsh mallow root per liter of extra virgin olive oil; a predefined quantity of *Amaranthus caudatus* seed extract; a predefined quantity of *Cynara scolymus* leaf extract; a predefined quantity of 25-36% concentration Citronellol and 10-18% concentration Geraniol; a predefined quantity of 100% concentration *Camellia oleifera*; a predefined quantity of 93-96% concentration Limonene; a predefined quantity of 10% concentration Apricot seed extract; and a predefined quantity of 20% concentration *Bambusa vulgaris* extract, and wherein said composition is in the form of a spray, an aerosol, or a serum.

2. The composition for a skin and hair product as claimed in claim 1 comprises:
the predefined quantity of solubilizer is 0.22% by weight of Polyglyceryl-6 Caprylate and Polyglyceryl-4 Caprate, and the predefined quantity of preservative is 0.07% by weight of benzyl alcohol Dehydroacetic Acid.

3. The composition for a skin and hair product as claimed in claim 1 comprises about 81.16% by weight of 100% fractionally distilled aloe vera liquid.

4. The composition for a skin and hair product as claimed in claim 1 comprises about 3.14% by weight of 2-3% concentration Marsh mallow Althea Officinalis root extract and about 0.15% by weight 10% concentration marsh mallow root per liter of extra virgin olive oil.

5. The composition for a skin and hair product as claimed in claim 1 comprises about 1.00% by weight of 25%-45% concentration Linalool, 20-40% concentration Linalyl acetate, and max 0.6% concentration camphor.

6. The composition for a skin and hair product as claimed in claim 1 comprises about 1.42% by weight hydrolyzed wheat protein.

7. The composition for a skin and hair product as claimed in claim 1 comprises about 0.15% by weight 20% concentration chamomille recutita matricaria flower extract.

8. The composition for a skin and hair product as claimed in claim 1 comprises about 0.21% by weight D-pantothenyl alcohol.

9. The composition for a skin and hair product as claimed in claim 1 comprises about 0.82% by weight 15-25% concentration z-α-Santalol.

10. The composition for a skin and hair product as claimed in claim 1 comprises about 0.24% by weight of 6-20% concentration g-Himachalene and 29-52% concentration b-Himachalene.

11. The composition for a skin and hair product as claimed in claim 1 comprises about 0.08% by weight hydrolyzed quinoa protein, and 0.10% by weight hydrolyzed keratin protein.

12. The composition for a skin and hair product as claimed in claim 1 comprises about 0.14% by weight propanediol, mel extract and about 0.17% by weight 10% concentration apricot seed extract.

13. The composition for a skin and hair product as claimed in claim 1 comprises about 0.08% by weight 99.7% concentration vegetable glycerin.

14. The composition for a skin and hair product as claimed in claim 1 comprises about 4.14% by weight Rosmarinus officinalis leaf extract, about 1.17% by weight *Cynara scolymus* leaf extract, and about 0.47% by weight *Linum alpinum* flower extract.

15. The composition for a skin and hair product as claimed in claim 1 comprises about 0.20% by weight (35-48% concentration limonene and 22-36% concentration linalyl acetate) and 0.58% by weight 93-96% concentration limonene.

16. The composition for a skin and hair product as claimed in claim 1 comprises about 1.28% by weight highly purified *Citrullus lanatus* extract.

17. The composition for a skin and hair product as claimed in claim 1 comprises about 0.48% by weight 20% concentration *Bambusa vulgaris* extract and about 0.15% by weight 100% concentration *Camellia oleifera*.

18. The composition for a skin and hair product as claimed in claim 1 comprises about 0.75% by weight 10:1 *Hibiscus* extract and propanediol.

19. The composition for a skin and hair product as claimed in claim 1 comprises about 1% by weight 10:1 red clover extract and propanediol and 0.42% by weight *Amaranthus caudatus* velvet flower seed extract.

20. The composition for a skin and hair product as claimed in claim 1 comprises about 0.21% by weight of 25-36% concentration citronellol and 10-18% geraniol.

* * * * *